United States Patent
Manske, Jr. et al.

(10) Patent No.: US 6,811,338 B1
(45) Date of Patent: Nov. 2, 2004

(54) DISPOSABLE SEMI-ENCLOSED APPLICATOR FOR DISTRIBUTING A SUBSTANCE ONTO A TARGET SURFACE

(75) Inventors: Thomas James Manske, Jr., Mason, OH (US); Dana Paul Gruenbacher, Fairfield, OH (US); James Herbert Davis, Middletown, OH (US); Gary Curtis Joseph, Cincinnati, OH (US); Piyush Narendra Zaveri, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 174 days.

(21) Appl. No.: 10/089,350

(22) PCT Filed: Oct. 10, 2000

(86) PCT No.: PCT/US00/27971

§ 371 (c)(1),
(2), (4) Date: Mar. 27, 2002

(87) PCT Pub. No.: WO01/26529

PCT Pub. Date: Apr. 19, 2001

Related U.S. Application Data

(63) Continuation-in-part of application No. 09/415,866, filed on Oct. 8, 1999, now Pat. No. 6,508,602.
(60) Provisional application No. 60/209,062, filed on Jun. 2, 2000, and provisional application No. 60/217,172, filed on Jul. 10, 2000.

(51) Int. Cl.[7] .......................... A47L 13/19; A61M 35/00
(52) U.S. Cl. .......................... 401/7; 15/104.94; 15/227; 401/133; 604/292
(58) Field of Search .......................... 401/7, 132, 133; 15/104.94, 227; 604/292, 306; 2/158

(56) References Cited

U.S. PATENT DOCUMENTS

| | | |
|---|---|---|
| 2,209,914 A | 7/1940 | Gerber et al. |
| 2,707,581 A | 5/1955 | Kaplan et al. |
| 2,790,982 A | 5/1957 | Schneider |
| 2,945,250 A | 7/1960 | Worthington |
| 2,961,677 A | 11/1960 | Zecchini et al. |
| 3,053,385 A | 9/1962 | Spees |
| 3,060,486 A | 10/1962 | Lewis |
| 3,324,500 A | 6/1967 | Fuller et al. |
| 3,485,562 A | 12/1969 | Hidden et al. |
| 3,608,708 A | 9/1971 | Storandt |
| 3,636,922 A | 1/1972 | Ketner |
| 3,757,782 A | 9/1973 | Aiken |
| 3,768,916 A | 10/1973 | Avery |
| 4,148,318 A | 4/1979 | Meyer |
| 4,430,013 A | 2/1984 | Kaufman |
| 4,510,640 A | 4/1985 | Omori |
| 4,537,819 A | 8/1985 | Schortmann et al. |
| 4,563,103 A | 1/1986 | Van Overloop et al. |

(List continued on next page.)

FOREIGN PATENT DOCUMENTS

| | | | | |
|---|---|---|---|---|
| DE | 3535926 A1 | 7/1987 | | |
| EP | 0 294 189 | 12/1988 | | |
| EP | 638277 A1 | * 2/1995 | .................. | 15/227 |
| GB | 2134371 A | * 8/1984 | .................. | 2/159 |

*Primary Examiner*—Gregory L. Huson
*Assistant Examiner*—Kathleen J. Prunner
(74) *Attorney, Agent, or Firm*—Peter D. Meyer

(57) ABSTRACT

A disposable, semi-enclosed applicator for distributing a substance onto a target surface is disclosed. The applicator has a first side, a second side, and an internal cavity between the first and second sides. The applicator is provided with at least one opening so that the internal cavity is externally accessible. Further, the applicator has a ratio of absorbency of the second side to the first side of at about 1.5.

20 Claims, 9 Drawing Sheets

U.S. PATENT DOCUMENTS

| | | | |
|---|---|---|---|
| 4,596,481 A | | 6/1986 | Tanaka |
| 4,600,620 A | | 7/1986 | Lloyd et al. |
| 4,696,593 A | | 9/1987 | Bayless |
| 4,759,084 A | * | 7/1988 | Madnick et al. ................ 2/158 |
| 4,759,472 A | | 7/1988 | Strenger |
| 4,762,124 A | | 8/1988 | Kerch et al. |
| 4,891,258 A | * | 1/1990 | Fahrenkrug ................. 428/138 |
| 4,902,283 A | | 2/1990 | Rojko et al. |
| 4,958,881 A | | 9/1990 | Piros |
| 5,008,969 A | | 4/1991 | Jarrett |
| 5,090,832 A | | 2/1992 | Rivera et al. |
| 5,100,028 A | | 3/1992 | Seifert |
| 5,127,127 A | | 7/1992 | Jarosinski |
| 5,195,658 A | | 3/1993 | Hoshino |
| 5,380,110 A | | 1/1995 | Festa |
| 5,411,178 A | | 5/1995 | Roders et al. |
| 5,441,355 A | | 8/1995 | Moore |
| 5,454,207 A | | 10/1995 | Storandt |
| 5,490,736 A | | 2/1996 | Haber et al. |
| 5,558,874 A | | 9/1996 | Haber et al. |
| 5,616,201 A | | 4/1997 | Finch et al. |
| 5,636,406 A | | 6/1997 | Strong |
| 5,681,574 A | | 10/1997 | Haber et al. |
| 5,829,089 A | | 11/1998 | Steadman |
| 5,957,605 A | | 9/1999 | Cohen et al. |
| 6,305,044 B1 | | 10/2001 | James et al. |
| 6,491,928 B1 | * | 12/2002 | Smith, III ................... 424/401 |
| 2002/0118993 A1 | * | 8/2002 | Lafosse-Marin et al. .... 401/201 |

* cited by examiner

DISPOSABLE SEMI-ENCLOSED APPLICATOR FOR DISTRIBUTING A SUBSTANCE ONTO A TARGET SURFACE

PRIOR APPLICATIONS

This application is a national stage application under 35 U.S.C. §371 and claims the benefit under 35 U.S.C. §365(c) of PCT application No. PCT/US00/027971 filed on Oct. 10, 2000, and published in English, which claims the benefit of U.S. application Ser. No. 09/415,536 filed Dec. 1, 1999 (now abandoned), which is a continuation-in-part of U.S. application Ser. No. 09/415,866 filed Oct. 8, 1999 (now U.S. Pat. No. 6,508,602 issued Jan. 21, 2003); and which claims the benefit of U.S. Provisional Application Ser. No. 60/209,062 filed on Jun. 2, 2000; and of U.S. Provisional Application Ser. No. 60/217,172 filed Jul. 10, 2000.

FIELD OF THE INVENTION

The present invention relates to a disposable semi-enclosed applicator useful for distributing substances onto target surfaces. More particularly, the present invention relates to such applicators wherein a substance may be applied to one side of the applicator material and distributed upon the surface of the target object, then removed from the surface and absorbed by the second side of the applicator.

BACKGROUND OF THE INVENTION

In the art of cleaning, a common approach involves dispensing a substance such as a cleaner or protectant from a bottle or other closed vessel onto the target surface, then utilizing a sponge, towel, brush, or other implement to distribute the product on the surface and, if desired, absorb any excess product, potentially with another implement or substrate. Such practices are commonplace with surfaces such as glass, countertops, and other kitchen and bathroom surfaces. While such practices are widely accepted, they often result in inefficient use of product and or contact with the substances involved. Moreover, utilizing such an implement typically only provides one type of material surface for use in contacting the substance and the target surface. Applying the substance to the applicator from a vessel at the point of use likewise often results in inefficient use of product since the product may be absorbed by the applicator and/or contact with the substances involved.

A common approach to cleaning glass or other surfaces, for example, is to spray cleaning solution onto the surface and then wipe the surface with a paper towel. Spraying the cleaning solution usually wastes some of the cleaning solution due to over-spray landing on areas not intended to be cleaned. This over-spray is often undesirable since some surfaces can be harmed by this cleaning solution or at a minimum requires additional surfaces to be cleaned. The paper towel is used to both spread the cleaning solution on the surface as well as absorbing any excess. The paper towel has a difficult time spreading the cleaning solution since it is typically designed to be highly absorbent. To compensate, a disposable paper towel can be made partially saturated making it easier to spread the cleaner. This however typically makes the towel weaker due to a paper towel's lack of wet strength. Then a separate dry paper towel can be used to buff the glass dry and to absorb any excess cleaner. This approach requires more cleaning solution to be applied and requires more paper towels than desired. To compensate for this approach some consumers use newspaper quality paper or low absorbency paper towels. This type of paper has a lower absorbency level and naturally does a better job of spreading the cleaning solution instead of absorbing the cleaner into the paper towel. Also these types of towels have a stiffer and harder furnish which tend to aid in buffing the glass to a streak-free shine. However, this approach is less desired because special paper towels are required and a lot of buffing is required to get the desired end result.

Accordingly, it would be desirable to provide a disposable applicator for applying a substance to a target surface that permits greater control by the user during the application process. It would also be desirable to provide such a disposable applicator which permits the user to apply a substance to a target surface with reduced messiness and waste of the substance. It would further be desirable to provide such a disposable applicator which provides multiple surfaces of diverse materials and or multiple substances for use in multiple tasks, and which did not require the user to manipulate, invert, or flip away a first surface before utilizing the second surface. It would further be desirable to have a disposable implement that had one side suitable for spreading cleaning solution with minimal effort and good wet strength and another side suitable for quickly absorbing any excess cleaner and buffing a surface to a streak-free shine. It would also be desirable to have a disposable applicator that eliminates over spray and avoids wasting cleaning solution. It would be further desirable to provide an applicator, such as a semi-enclosed applicator, which protects the users hands from contact with liquids and other materials used to treat the target surface during application and/or removal of the liquid or other material.

A variety of semi-enclosed applicators are known in the art. U.S. Pat. No. 5,807,296 issued to Tommy Stubbs on Sep. 15, 1998, U.S. Pat. No. 5,864,883 issued to Patricia Reo on Feb. 2, 1999, and U.S. Pat. No. 5,649,336 issued to Valerie Finch, et.al. on Jan. 22, 1997 disclose semi-enclosed applicators with at least one absorbent portion but are not ideally adapted for both spreading or applying fluid, and then separately absorbing or removing it.

U.S. Pat. No. 5,979,007 issued to Min Tet Soon on Nov. 9, 1999 discloses a non-disposable applicator having more than one layer of material for treating a target surface, where a first layer must be flipped away in order to utilize the functionalities of the second layer.

U.S. Pat. No. 5,373,601 issued to Dennis Miller on Dec. 20, 1994 discloses a semi-enclosed applicator in the form of a nonabrasive tubular sleeve (such as lambs wool) with a perpendicularly oriented abrasive surface.

U.S. Pat. No. 4,807,322 issued to Tomislav Littledeer on Feb. 8, 1989 discloses a non-disposable automobile windshield cleaning mitt with a chamois-like surface and other functional extensions.

U.S. Pat. No. 5,134,746 issued to Steven William on Aug. 4, 1992 discloses another non-disposable cleaning mitt with both a non-absorbent and an absorbent side. U.S. Pat. No. 3,806,260 issued to Hobson Miller on Apr. 23, 1974 and U.S. Pat. No. 3,793,121 disclose cleaning mitts for applying polishing materials, such as shoe shine material, having an applicator means on one side and a polishing means on the opposite side. While such mitts may be useful for applying materials intended to remain on or absorbed into a target surface, they are not intended for absorbing excess liquid that may be useful in treating or cleaning the target surface

SUMMARY OF THE INVENTION

The present invention provides a disposable, semi-enclosed applicator for distributing a substance onto a target surface. The applicator has a first side, a second side, and an internal cavity between the first and second sides. The applicator further includes at least one opening, such that the internal cavity is externally accessible. In a preferred embodiment, the first side comprises a porous sheet containing at least 50%, by weight, non-absorbent material, the second side comprises an absorbent sheet containing at least 50%, by weight, of cellulosic material; and the applicator further comprises a substantially fluid-impervious barrier layer within said internal cavity adjacent the first side.

In another preferred embodiment, the first side comprises a porous non-absorbent sheet having a basis weight of no greater than about 100 gsm, the second side comprises an absorbent sheet having a basis weight of no greater than about 140 gsm, and the applicator further comprises a substantially fluid-impervious barrier layer within said internal cavity adjacent said first side. The applicator preferably has a Ratio of Absorbency of said second side to said first side of at least about 1.5.

In general, the first side and the second side of the applicators hereof will preferably be of planar geometry and be essentially parallel to one another. By essentially parallel what is meant is that the plane of the sides will be either exactly parallel or if not exactly parallel, will depart from being exactly parallel by an extent suitable to allow the user to insert ones hand, finger, or other body part into the cavity of the applicator.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements, reference numerals with the same final two digits identify corresponding elements, and wherein:

DETAILED DESCRIPTION OF THE INVENTION

Figure 1:
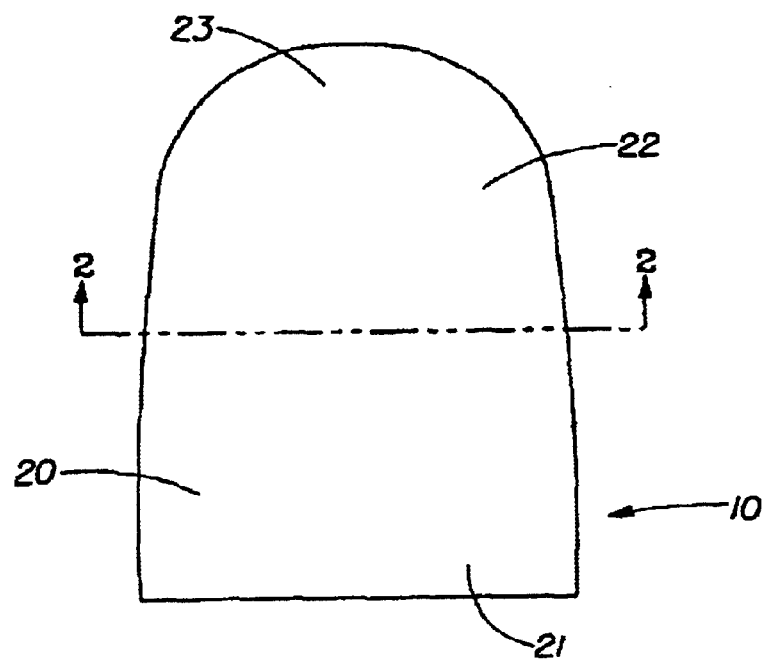
FIG. 1 is a plan view of a preferred embodiment of a semi-enclosed applicator in accordance with the present invention, in the form of a mitt.

As used herein, the term "hand article" refers to a covering for the hand or portion of the hand such as a finger or thumb. The term "disposable" is used herein to describe band articles that are not intended to be restored or reused (i.e., they are intended to be discarded after a single use or a limited number of uses (typically three or less), and preferably, to be recycled, composted or otherwise disposed of in an environmentally compatible manner. As used herein the term "glove" refers to a covering for the hand having separate sections for each finger. As used herein, the term "mitt" refers to a covering for the hand having an enclosure that leaves the fingers unseparated and that may include space for the thumb in the main enclosure or may provide space for the thumb in a separate enclosure for the thumb or may not include a thumb enclosure at all. This term is also applicable to an apparatus which covers only one or more digits of a user, such as in the case of a "finger mitt" as described below. While the terms "glove" and "mitt" have been defined with respect to the human hand, similar structures could be utilized to cover or enclose other elements of human anatomy, such as foot coverings, or other items for which coverings of a particular shape are preferred.

As used herein, the terms "absorb" and "absorptive" refer to the ability of a material to retain liquid under an applied force (e.g., hand pressures such as compression or squeezing, centrifugal forces, etc.). In general, absorptive materials useful herein will absorb liquids by swelling (e.g., cellulosic materials), chemical bonding and/or enclosing liquids in an internal reservoir structure (e.g., natural fibers such as cotton). "Absorptive" does not generally refer to liquids entrapped in interstitial voids located between distinct structural elements of a material or structure. The absorptive properties of materials referred to herein will be determined according to ASTM D2654-89a "Standard Test Methods for Moisture in Textiles," which determines moisture regain (the amount of water resorbed, at a standard atmosphere for testing, by the material divided by the mass of the dried material.) ASTM D1909-96 "Standard Table of Commercial Moisture Regains for Textile Fibers" lists formally adopted moisture regain percentages for various materials. "Absorbency" as used herein is the moisture regain.

As used herein the term "substantially non-absorbent" refers to a material or structure composed on a weight basis of a majority (at least 50% by weight) of nonabsorbent fibers or material. As used herein the term "substantially absorbent" refers to a material or structure composed on a weight basis of a majority (at least 50% by weight) of absorbent fibers or material. As used herein, an "absorbent fiber" or "absorbent material" refers to a fiber or material having an Absorbency of at least 5.0%. A "nonabsorbent fiber" or "nonabsorbent material" refers to a fiber or material having an Absorbency of less than 5.0%. For example, a nylon fiber or material, with an Absorbency of 4.5%, is considered non-absorbent. A cellulose acetate fiber or material, with an Absorbency of 6.5%, is considered absorbent.

As used herein, a "sheet" refers to a planar structure that, without limitation, can be the form of a web or a film.

As used herein the term "extension force" refers to forces applied by hand movements to a surface to extend and/or bend that surface linearly and/or curvilinearly. The term "semi-enclosed applicator" is intended to refer to an applicator device having at least one externally accessible internal cavity for receiving a portion of human anatomy such as a hand or finger so that the applicator device may be used as an implement. A glove, mitt or finger mitt would be an example of such a semi-enclosed applicator in the context of the present invention.

Applicator Construction and Operation

A representative embodiment of a semi-enclosed applicator of the present invention in the form of a hand article is the disposable mitt 10 shown in FIG. 1. FIG. 1 is a plan view of the mitt 10 of the present invention in its flat-out state illustrating the body portion 20, cuff portion 21, central portion 22, and distal portion 23. In general terms, the mitt 10 has an internal cavity which is accessible through an opening in the cuff portion and extends inwardly to the distal portion which is closed.

Figure 2:
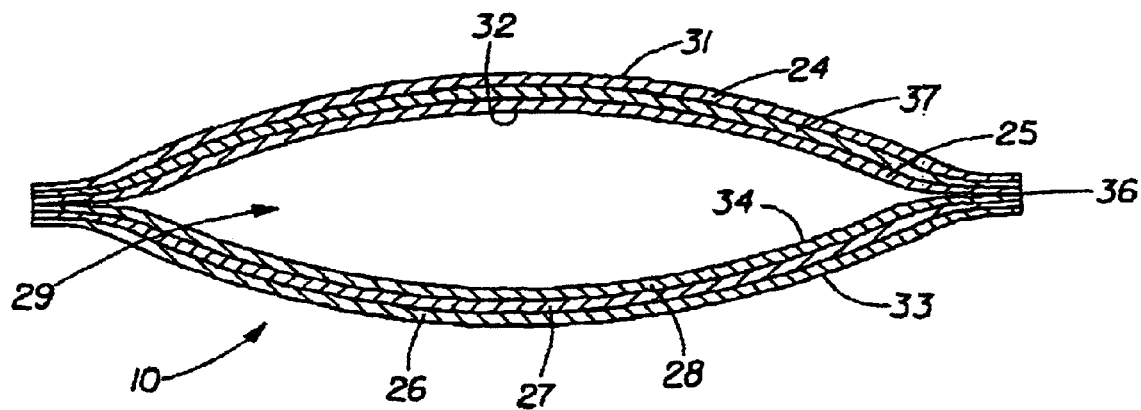
FIG. 2 is a cross-sectional view of the mitt of FIG. 1 taken along line 2—2.

FIG. 2 shows more specifically the construction details of the mitt 10. The mitt 10 has a front outer surface 31, a front inner surface 32, a back outer surface 33, and a back inner surface 34. The front and back inner surfaces define a hollow interior 29 into which a hand may be inserted through an opening in the cuff portion 21. The mitt 10 includes a front panel 24, which defines the front outer surface 31, and a back panel 26 which defines the back outer surface 33. The front and back panels are connected along their periphery to form a seam 36.

The seam 36 can be straight or may be tapered. For example, the seam 36 may be inwardly tapered in the area of the cuff region to allow the applicator to stay on the hand of the user better. In addition to, or in place of, tapered seams, elastic material may be added in the cuff region to keep the applicator on the hand of the user.

In accordance with the present invention, the front panel 24 comprises a porous sheet, such as a fibrous nonwoven web material. In order to provide for residence time of the liquid upon the target surface, the material utilized for the front panel 24 is preferably substantially non-absorbent. Non-absorbent fibers of a nonwoven, for example, do not take up water and thus do not swell when exposed to water. Examples include polyolefin (i.e. polyethylene, polypropylene) and polyester fibers. In place of non-absorbent fibers, an apertured film or web can also be used as a porous, non-absorbent material. Examples of materials of interest include nonwoven, apertured film, absorbent or fibrous absorbent material, or laminates and/or combinations thereof. The nonwovens may be made by but not limited to one of the following methods: spunlace, spunbound, meltblown, carded, airlaid, and hydroentangled. One such material sufficient in durability and strength to provide a robust cleaning surface is a spunbond polypropylene nonwoven such as from BBA Nonwovens of Simpsonville, S.C. Other structures such as hydroentangled materials comprising cellulose, rayon, polyester, and any combination thereof may also be used. One such set of materials are made by Dexter Corporation of Windsor Locks, CT and sold under the trade name Hydraspung®. One skilled in the art will understand that a wide range of materials can be used as long as the material of interest provides the required durability to complete the cleaning task.

The fiber diameter is ideally less than about 100 microns, more preferably less than about 50 microns and yet even more preferably in the range from about 10 microns to about 35 microns. A higher number of smaller diameter fibers will aid in holding onto dirt via mechanical entanglement and also yields a softer substrate.

The basis weight of the first side of the applicator hereof (the nonabsorbent side), or the front panel 24 as shown for example in FIG. 1, should generally be about 100 grams per square meter (hereinafter "gsm") or less, preferably about 75 gsm or less, more preferably about 55 gsm or less, most preferably about 45 gsm or less. Basis weight is typically at least about 10 gsm for practical reasons, more typically at least about 15 gsm, preferably at least about 25 gsm.

Optionally the fibers are also hydrophobic, oleophillic, and positively charged which aid in holding onto dirt, oils and other contaminants that are desired to be removed from the surface. An oleophillic material that oils naturally attach themselves to is preferred. Preferably the fibers maintain their positive charge even when wet. One approach to achieve this positive charge is to coat the fibers with a treatment of a cationic polymer such as polyacrylanide (PAM), polyethylenimine (PEI), polyvinylpyrrolidone (PVP), polyamide epichlorohydrin (PAE). A PAE resin, produced by Hercules under the tradename Kymene® is one such material. For a glass cleaning and general multiple purpose surface cleaner example polypropylene or poylethylene non-wovens have been found to be good materials for applying a cleaning formula to glass, shiny surfaces and other surfaces. The non-woven does not swell with the cleaner and releases the cleaner when rubbing with minimal retention as compared to a disposable paper based towel. The thermoplastic non-woven has good wet strength and has adequate scrubbing capability without scratching the surface to be cleaned. The non-woven also has a low coefficient of friction that allows the substrate to glide very easily across the surface to be cleaned with minimal effort and good ease of spreading the cleaning solution.

In view of the fact that polypropylene nonwovens, and many other suitable materials for front panel 24, are highly porous and rapidly penetrated by liquids, the mitts of the present invention optionally include a sheet of a substantially absorbent material 37 (e.g. a tissue paper layer) between the barrier film 25 and the front panel 24. This sheet of substantially absorbent material is preferably capable of wicking the liquid of interest to a large surface area of the outer layer (front panel 24). Depending upon the viscosity of the liquid and the desired surface area to supply the liquid, sheets with different capacities and wicking rates can be used to control liquid distribution. The basis weight of such sheet 37, preferably tissue paper, is typically about 60 gsm or less, preferably about 40 gsm or less, and yet even more preferably in the range of from about 10 to about 30 gsm. One suitable material is a single ply of a disposable kitchen paper towel such as Bounty®, a product of the Procter & Gamble Company. If it is desired to have slower fluid transport, higher capacity materials such as two ply Bounty® can be used. If it is desired to have faster fluid transport, less absorbent materials such as Cellu Tissue 7020, a product of the Cellu Tissue Corporation of East Hartford, Conn. can be used as well as creped or other corrugated materials which aid in fluid transport. Those skilled in the art will understand that the tissue material can be chosen from a wide range of tissues so as to best meet the required capacity and wicking rate for a given embodiment.

Yet another method that can be employed to control liquid distribution onto the outer layer 24 is the patterning of adhesives into an array of lines, spirals, spots, or any other open pattern network of filaments to combine outer layer 24 to sheet 37, to combine sheet 37 to fluid impervious barrier layer 25, to combine sheet 37 to fluid impervious barrier layer 25. In a preferred embodiment, it has been found to be advantageous when the applicator contains vertical corrugations, described later, that the adhesive be applied in an array of horizontal lines. These horizontal lines can be applied using slot coating hot melt equipment as well as spray hot melt applicators with the air turned off. While not wanting to be bound by theory, it is believed that the presence of horizontal adhesive beads channels the liquid in the horizontal direction while the vertical corrugations channel the liquid vertically. Thus, the combination of these channeling mechanisms allows liquid to be distributed at the same time in both the horizontal and vertical directions. Depending upon the desired liquid distribution for a given embodiment, the spacing of the adhesive lines can be changed. In a preferred embodiment, these adhesive lines are spaced from about 1 mm to about 10 mm apart, more preferably from about 2 mm to about 5 mm apart. The adhesive type and basis weight is dependent on the two materials being combined, compatibility with the liquid of interest, and the processing method. The adhesive basis weight will preferably be less than about 12 gsm, more preferably from about 0.1 gsm to about 8 gsm. The adhesive type can be any of the type of water-based, solvent-based, hot melt, pressure sensitive, or others known in the art. For the preferred embodiment, a pressure sensitive adhesive made by Ato Findlay of Wauwatosa, Wis., product H2031, provides adhesion for combining layers 24 to 37 and layers 37 to 25. Other methods of patterning adhesives include gravure printing the adhesive into channels that direct the fluid flow. In combination or in place of adhesives, the attachment means to combine layers 24, 37, and 25 may comprise pressure bonds, ultrasonic bonds, mechanical bonds, or any other suitable attachment means or combinations of these attachment means as are known in the art. In the same way adhesives can be applied to direct the fluid wicking, these bonding methods can create channels in the desired direction for fluid flow. While not wanting to be bound by theory, it is believed these channels are created when materials are heated in discrete areas effectively creating a seal that liquid cannot pass through and thus must flow around.

In order to protect the hand of the user from contact with the liquid during the dispensing and dispersing operation, the mitts of the present invention include a substantially fluid impervious barrier layer 25, the interior of which defines the front inner surface 32 that faces the wearer's hand during use. The barrier layer is made from a water impervious material. By substantially fluid impervious what is meant is that water of other fluids of the type intended for use with the applicator hereof cannot penetrate through one side of the barrier layer to the other during the elapsed time period of intended use. Suitable barrier materials include polymer films (i.e. polyethylene, polypropylene, EVA, and polymer blends or coextrusions), which may be rendered extensible by methods to be described hereafter. The barrier layer, whether or not rendered extensible, can be textured by any means known in the art, including but not limited to, embossing, ring-rolling, and incremental staining, Materials which are embossed, whether or not rendered extensible, provide improved tactile properties and greater control over the applicator in terms of contact and coefficient of friction with the hand. Preferably, the material and the surface alteration are made such that the coefficient of friction between the inner surface 32 and a wearer's hand is greater than the coefficient of friction between the outer surface 31 and the target surface. This reduces the likelihood that the mitt 10 may slip or rotate inadvertently in use. The barrier layer can be combined with another "softness enhancing" material that provides additional comfort, softness and tactile feel to the user's hand on the front inner surface 32. Such materials can include, but are not limited to, fibrous (natural, synthetic, or combination thereof) or foamed materials.

After the liquid product has been spread onto the target surface, it is typically desirable to absorb and remove excess liquid, contaminates and/or particles from the target surface while minimizing filming, streaking and residuals. Accordingly, the second side of the mint (i.e., referring to the figures—the back panel 26 of the mitt 10) comprises an absorbent sheet. Preferably the absorbent sheet is composed of substantially absorbent material. The preferred materials for incorporation into the absorbent sheet include fibrous materials, especially absorbent fibers at levels of at least 50% by weight of the absorbent sheet. Examples include man-made fibers derived from cellulose (i.e. rayon, cellulose acetate, cellulose triacetate) and natural cellulose fibers (i.e. derived from paper pulp, e.g., from trees or other vegetative sources). Other examples of absorbent materials include particles and fibers made from superabsorbent polymers (e.g., partially crosslinked copolymers of acrylic acid/ acrylates) that can be incorporated into back panel 26. Examples of materials of interest for the back panel 26 include nonwoven, apertured film, absorbent or fibrous absorbent material, superabsorbent polymer fibers or powders, or laminates and/or combinations thereof. The nonwovens may be made by but not limited to one of the following methods spunlace, spunbound, meltblown, carded, air-laid, and hydroentangled. The basis weight of the second side (i.e. the back panel 26 of the figures) of the applicator hereof, should be no greater than about 140 gsm, preferably no greater than about 120 gsm, more preferably no greater than about 100 gsm. Typically, for practical reasons, the basis weight will be at least about 10 gsm, preferably at least about 25 gsm, more preferably at least about 40 gsm, even more preferably at least about 60 gsm, and most preferably at least about 80 gsm.

In one embodiment, four plies of disposable kitchen paper towel such as BOUNTY®, a product of The Procter & Gamble Company, has been found suitable for use. This paper towel material typically has the capacity to absorb between about eight and about nine times its own weight in water and its fibers will swell to retain the liquid. If higher wet strength is desired, other structures such as hydroentangled materials comprising cellulose, rayon, polyester, and any combination thereof, may provide enhanced strength. One such set of materials are made by Dexter Corporation of Windsor Locks, Conn. and sold under the trade name Hydraspun®. Additional additives such as wet strength additives, dry strength additives, cationic treatments, cationic promoters, softeners and absorbency aids may be employed if desired. Further, due to evaporation, absorption into the target surface, and other effects, however, the back panel often is not expected to absorb the entire quantity of liquid spread onto the target surface.

As described above, in one embodiment one side of the applicator is designed with a majority of non-absorbent fibers (termed "substantially non-absorbent" material or fibers) and the other side is designed with a majority of absorbent fibers (termed "substantially absorbent" material of fibers). Most preferably the absorbent side of the applicator hereof is composed of substantially absorbent material, the absorbent component of which are cellulosic material or, especially, cellulosic fibers. In the context of the invention, these terms are relative to one another. Depending on the specific application, the liquid to be spread, environmental conditions, and the benefits sought, the amount of liquid that the substantially absorbent side and the amount of liquid the substantially non-absorbent side take up will not be a constant. Rather the substantially absorbent side will always have a higher absorbent capacity than the substantially non-absorbent side.

The Ratio of the Absorbency of the second side, i.e. the absorbent side, of the applicator hereof to the first side, i.e., the nonabsorbent side, is preferably at least about 1.5, more preferably at least about 2, even more preferably at least about 4.

In some instances it is preferable to have multiple layers on either the front side (24) or the backside (26) to provide additional absorbency and/or cleaning surfaces. Preferably additional layers can be heat sealed only to the perimeter and sealed in such a way that the layer is peelable. However, layers may be attached and removed by other methods such as perforations, peelable adhesives, and the like. The layers can be slightly offset at the cuff region (21), or additional material such as tabs may protrude from the layer, making it easier for the user to remove one layer at a time. Peelable heat seals may be accomplished by heat sealing the individual layers at a lower temperature or with less seal time such that a peelable seal occurs. These layers can also be made peelable by using a contamination layer or other methods known in the art. An example of how peelable layers can be used would be for a heavy-duty glass cleaning mitt where heavily soiled surfaces are cleaned. On heavily soiled surfaces, it has been seen where the mitt surfaces 24 and 26 become soiled to an undesirable level prior to complete use of all the fluid in the reservoir is used. To overcome this, an extra layer(s) of a polypropylene nonwoven could be used on the wet cleaning side allowing the user to peel off a dirty layer as needed to deliver a fresh new clean wet scrubbing layer. Similarly, the absorbent back panel 26 could have multiple layers of an absorbent paper towel such as Bounty® made by Procter & Gamble. The absorbent backside layers could be coated with a thin coating of a barrier material such as polyethylene or polypropylene that prevents fluid from saturating other layers except for the outer layer that is being used. When this outer layer becomes too wet or too dirty, the outer layer can be removed exposing a new clean layer.

To protect the wearer's hand from contact with liquids absorbed by the back panel 26, it may be desirable for some applications to include an optional additional fluid impervious barrier layer 27, the interior of which defines the back inner surface 34 that faces the wearer's hand during use. Suitable barrier materials include polymer films (i.e. polyethylene, polypropylene, EVA, and polymer blends or coextrusions), which may be rendered extensible by methods to be described hereafter.

The interior surfaces of the mitt, particularly the back inner surface 34, may be optionally provided with friction-enhancing elements or coatings 28 to prevent slippage between the wearer's hand and the back inner surface, which could lead to rolling or rotating of the mitt upon the hand when the frictional forces between the back panel and the increasingly dry target surface escalate. Suitable materials that can be used as the friction-enhancing elements include rubber, thermoplastic elastomers (e.g., KRATON® produced by Shell Chemical Company), polyolefins with ethylene vinyl acetate or alpha-olefin copolymers, and polyolefin plastomers (e.g., Affinity® produced by Dow Chemical of Midland, Mich. and Exact® polyolefin plastomers produced by Exxon Chemical of Houston, Tex.). In one preferred embodiment, for example, a hot melt coating produced by Ato Findlay of Wauwatosa, Wis. under the designation of product 195-338, can be slot coated onto the back inner surface 34. The coating can also be applied in a foamed state such as by the addition of physical blowing agents such as nitrogen and/or carbon dioxide. In addition to slot coating, suitable materials can be applied (foamed or unfoamed) in one or more of an array of lines, spirals, spots and/or any other patterned network, by spraying, gravure printing, or by adhesively or otherwise securing separate pre-formed elements.

In one particularly preferred embodiment, the back inner surface 34 has a friction-enhancing element that has a higher coefficient of friction between its surface and the wearer's hand than the coefficient of friction between the outer surface 33 and the target surface. In a glass cleaning implement, for example, the back panel 26 may be an absorbent paper towel material used to absorb the liquid and buff the target surface dry after it is cleaned. The coefficient of friction between a glass surface with Cinch® window cleaner, a product of The Procter & Gamble Company located in Cincinnati, Ohio, and a paper towel may be in the range from about 0.7 to about 0.9 as measured according to ASTM D1894-90, entitled "Standard Test Method for Static and Kinetic Coefficients of Friction of Plastic Film and Sheeting." A preferred friction-enhancing element in this embodiment would thus be a coating that delivers a higher coefficient of friction between a wearer's hand and the back inner surface 34 of the mitt 10 such that the mitt 10 does not slip or rotate on the hand when buffing the target surface with the back panel 26.

Figure 6:
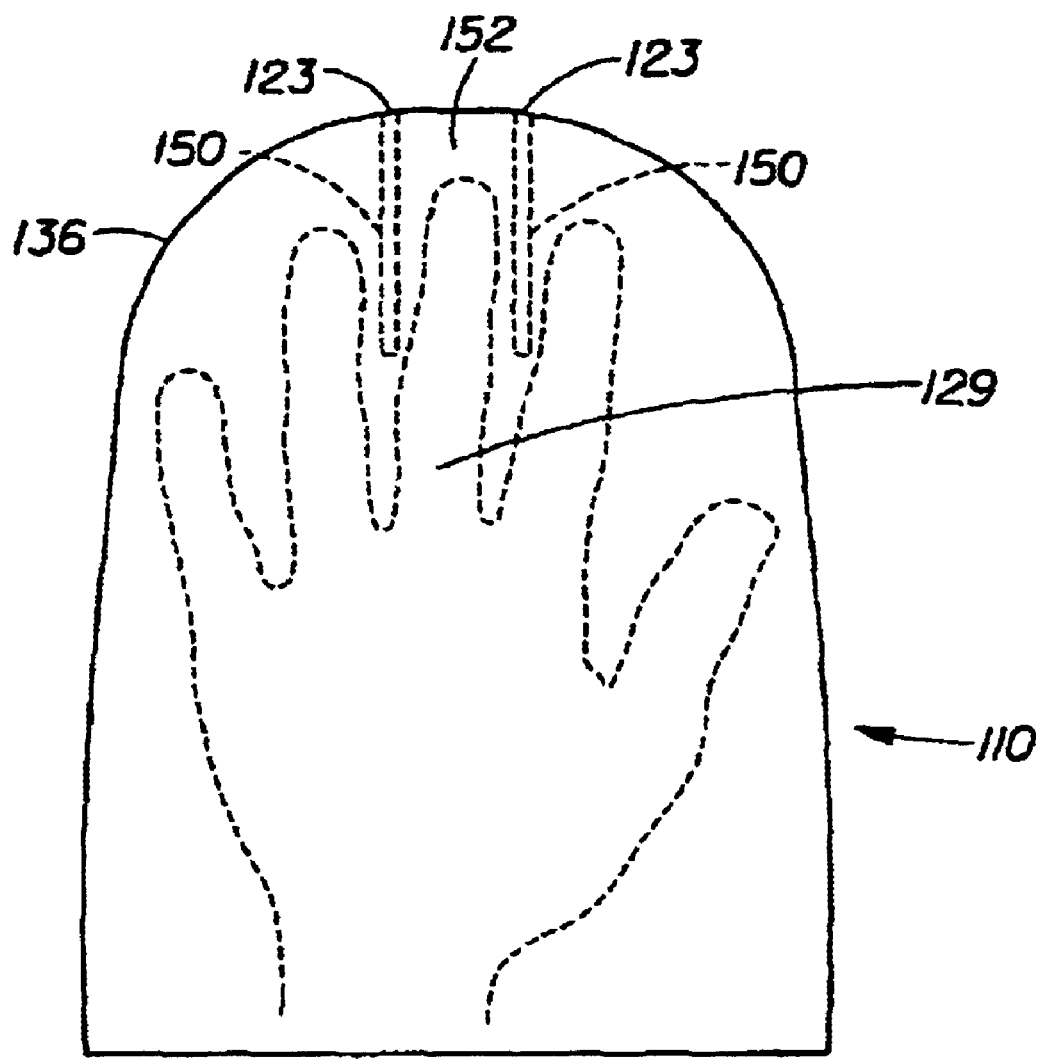
FIG. 6 is another plan view of a preferred embodiment with internal pockets to separate fingers within a mitt.
Figure 7:
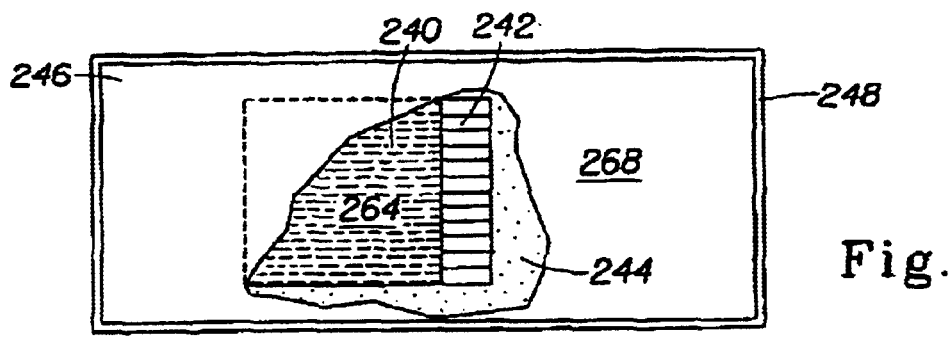
FIG. 7 is a top view of a temperature changing element of one embodiment of the present invention.

Alternatively, as shown in FIG. 6, the mitt 110 can be bonded or combined with one or more seals to provide a full or partial pocket for one or more fingers of the user. The line seal 150 may prevent the mitt 110 from rotating on the hand of the user, and may further provide a means for gripping the mitt when the fingers are pressed together during use. The line seal 150 may form a partial pocket 152 for one or more fingers and may, for example, extend from the outside perimeter 136 at the top 123 of mitt 110 towards the central portion 129. In one embodiment, the line seal may extend a distance from about 2 inches to about 4 inches from the outside perimeter 136 of the mitt 110.

In use, a wearer of the mitt 10 inserts a hand into the hollow interior through the provided opening at the cuff region 21 wherein the back panel contacts the back of the wearer's hand and the front panel contacts the wearer's palm. As the construction of the mitt 10 is more generic than a glove with defined anatomically-conforming geometry, the mitt may be used for either hand and/or may be appropriately sized to fit the foot of a wearer or any other bodily extremity.

If desired, at the end of its use, the mitt can be everted by making a fist with the mitt-hand, pulling the structure over the fist from the cuff region 21 of the mitt 10. Thus the layers are transposed, and the inner surface of the front panel and the inner surface of the back panel become the outer surfaces of the now waste article. More simply stated, the mitt is turned inside out after its use and then thrown away. That is, the wearer makes a fist, and with his or her other hand, grasps a point on the cuff region and carefully pulls the fisted hand toward the open mouth of the mitt, until the entire end of the mitt is pulled through the cuff.

In a preferred embodiment, the mitt 10 is a differentially extensible hand article wherein at least a portion of the glove extends and/or contracts about a wearer's hand and/or wrist without the use of traditional elastic such as natural or synthetic rubber. By the term "differentially extensible" or "differential extensibility" it is meant herein to describe that quality of extensibility wherein portions of the glove extend or contract independently of other portions in response to varying hand sizes and motions. Preferably, this differential extensibility allows a range of hand sizes to fit comfortably within the mitt The mitt 10 may be provided with differential extensibility by utilizing a structural elastic-like film web such as those described in commonly-assigned U.S. Pat. No. 5,518,801, issued to Chappell, et al. on May 21, 1996, and U.S. Pat. No. 5,650,214, issued Jul. 22, 1997 in the names of Anderson et al., and commonly-assigned, co-pending U.S. patent application Ser. No. 08/635,220, filed Apr. 17, 1996 in the names of Davis et al., entitled "Fitted Glove", the disclosures of each of which are hereby incorporated herein by reference. Alternatively, differential extensibility to fit varying sized hands comfortably can be accomplished by various elastic-like materials, composite materials that produce elastic-like characteristics and/or processes to make a material(s) more elastic-like. Examples of suitable elastic-like materials include low density polyolefins such as low density polyethylene, linear low density polyethylene, ultra low density ethylene copolymers (copolymerized with alpha-olefins such as butene-1, octene-1, hexene-1, etc.), Affinity® polyolefin plastomers produces by Dow Chemical Company of Midland, Mich. and Exact® polyolefin plastomers produced by Exxon Chemical of Houston, Tex. As used herein, the term "elastic-like" describes the behavior of web materials such as web materials which, when subjected to an applied elongation, extend in the direction of applied elongation. Also, when the applied elongation is released the web materials return, to a substantial degree, to their untensioned condition. The term "web" as used herein refers to a sheet-like material comprising a single layer of material or a laminate of two or more layers.

Figure 3:
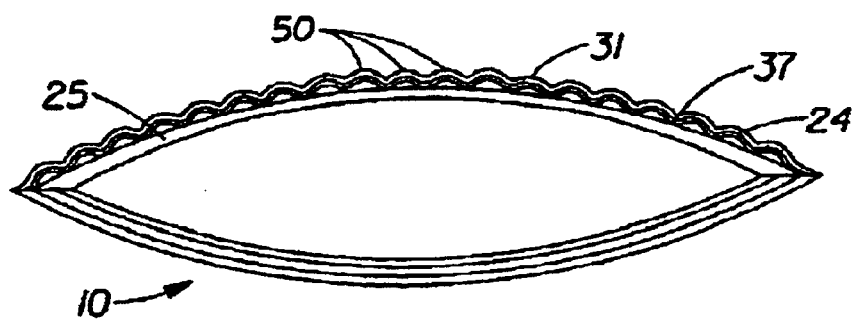
FIG. 3 is a cross-sectional view of an applicator similar to that of FIGS. 1 and 2, but illustrating the use of rugosities on at least one surface.

The use of differentially extensible materials and suitable manufacturing processes, such as those described below, may be utilized to create a corrugation or pleating of at least one surface of the applicator, also characterized as a plurality of "rugosities". FIG. 3 illustrates a cross-sectional view of an applicator similar to that of FIGS. 1 and 2, but depicting the use of rugosities on an applicator surface. The applicator 10 of FIG. 3 is structurally similar to the cross-sectional view of FIG. 2, and therefore many of the reference numerals are omitted in the interest of clarity. However, as shown in FIG. 3, the fluid-impervious barrier layer 25 is provided with differentially extensible properties, preferably in accordance with the aforementioned commonly-assigned U.S. patents to Chappell, et al., and Anderson, et al., and therefore provides a plurality of rugosities 50 to the front outer surface 31 via the pleating or corrugation of the tissue layer 37 and front panel 24. The size and frequency of the corrugations and/or pleats can be controlled, in one embodiment, by the bonding pattern and the amount of stretch applied. The greater the stretch applied to the barrier layer 25, the greater the amount of material will be available for the corrugations and/or the pleats. In addition, the bonding pattern between a stretched material and the unstretched tissue layer 37 and/or the front panel 24 can be used to control the frequency and location of the corrugations and/or pleats. Such rugosities would be, in the embodiment of FIG. 3, parallel pleats or corrugations which extend in the direction into and out of the page. Without wishing to be bound by theory, it is believed that such corrugations or rugosities enhance the scrubbing and dispersing performance of the front outer surface and may provide built-in void space for trapping dust, dirt, and particulate material. The direction of the corrugations, for example, can be used to control liquid flow and have proven to be effective in preventing liquid from running off the mitt in cases of overdosing by the user. Liquid will naturally follow the direction of the corrugations preferentially versus spreading across the corrugations. Thus corrugations that run along the length of the mitt will tend to move the liquid along the length of the mitt. This also prevents the liquid from running off the narrower width side when the mitt is held at an angle. The corrugations can also act as baffles such that liquid sitting on the surface will not spread across the baffles but instead will tend to travel in the direction of the baffles. Consequently the pattern, direction, and frequency of these corrugations can be controlled and designed to spread the liquid as desired. The texture of the extensible film also provides a better aesthetic feel to the hand and provides an elastic fit desired in a glove or mitt.

Figure 4:
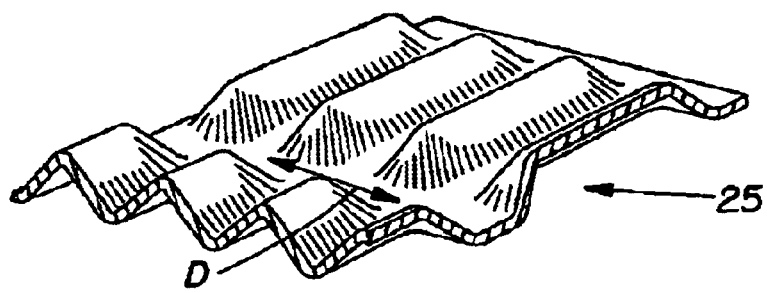
FIG. 4 is a partial perspective view of one material useful in forming the rugosities of FIG. 3.

FIG. 4 is a perspective view of one suitable material and structural configuration for a barrier layer 25 in accordance with FIG. 3, such material being consistent with the materials disclosed and claimed in the aforementioned commonly-assigned U.S. patents to Chappell, et al., and Anderson, et al. Such materials typically provide for extensibility, and (if applicable) elastic recovery, in a predominant direction illustrated via the use of the arrow labeled "D" in FIG. 4. When such a directional material is utilized in the construction of an applicator consistent with FIG. 3, the direction "D" would be oriented perpendicular to the direction in which it is desired for the rugosities to extend. Said differently, for the embodiment of FIG. 3 the direction "D" for the barrier layer 25 is left to right across FIG. 3 while the rugosities 50 extend in the direction into and out of the page. The embossed pattern of the film further provides better aesthetics and hand feel by allowing more air to circulate around a wearer's hand and thus deliver a cooling effect that is not available with a flat film.

Figure 5:
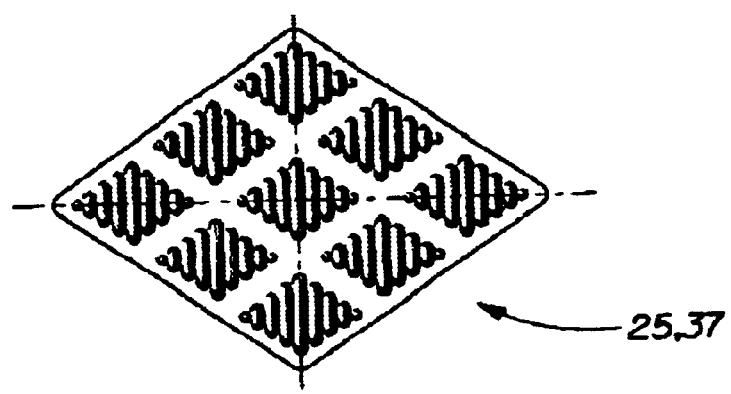
FIG. 5 is another material useful in forming the rugosities of FIG. 3.

The method to obtain rugosities described above results from an extensible web that is stretched, bonded to an unstretched web (either the front panel 24 or a laminate of front panel 24 and tissue layer 37) and allowed to relax to create rugosities. Another way of making either the first or second side of the applicator having more surface area without increasing the footprint of the applicator is to texture or reform the web into pleats, ribs, corrugations, and the like in any method known in the art. Such methods include but are not limited to embossing, ring-rolling, and incremental straining. The web can be a single layer of material or a lamination of several layers of material. For example, as shown in FIG. 5, the front panel 24, such as a polypropylene nonwoven, and the barrier layer 25, such as a polyethylene film, can be textured and made extensible in accordance to the approach described in the aforementioned Chappel patent. Optionally, a tissue layer 37, such as a 1 ply of Bounty® paper towel, can be added between layers 24 and 25 when the laminate is textured. These layers can be bonded by but not limited to any of the following bonding methods: thermal bonding, sonic bonding, adhesive bonding (using any of the number of adhesives including but not limited to spray adhesives, hot melt adhesives, latex-based adhesives, water-based adhesives, and the like), and directly applying nonwoven fibers onto a substrate. In a preferred embodiment, the materials are adhesively bonded with a hot melt adhesive. One such adhesive is H2031, a product Ato Findlay of Wauwatosa, Wis. While not wanting to being bound by theory, it is believed that the thermoplastic elastomer properties of the adhesive aid in allowing the materials to deform to the desired shape and aid in setting the materials into the desired shape thus allowing thicker pleats and pleats more resistant to compressive forces.

Applicators in accordance with the present invention may find utility in many situations. An example of an applicator made in accordance with the present invention would include a glass cleaning mitt provided as a flexible structure for distributing glass cleaning substance onto a target glass surface. The mitt might preferably include a layer of ws polypropylene spunbonded nonwoven material for providing a substrate for spreading the cleaning substance and scrubbing such surface with the cleaning solution. Such spunbonded nonwoven is commercially available such as from BBA Nonwovens of Simpsonville, S.C. This material would also preferably be substantially free of surfactants or other treatments that might leave residual material on the surface being cleaned. Successful application occurs when a portion of the deposited substance subsequently coats a portion of the target surface where the substance was not originally deposited. Upon removal of the non-absorbent material from the target surface, at least some of the substance remains located on the target surface, preferably in a substantially-uniform fashion. For glass cleaning, a suitable absorbent material for removing dirt, debris, and excess cleaner, might be 4 ply Bounty(paper towel, a product of the Procter and Gamble Company. The cleaning solution can be applied directly to the target surface, spread by the substantially non-absorbent side, and buffed to a streak-free shine by the absorbent side. Alternatively, the cleaning solution can be applied directly to the nonabsorbent side of the applicator to eliminate overspray of product onto areas near the target surface.

The mitts can be used for cleaning glass surfaces including but limited to, inside and outside windows, mirrors, television screens, tables, and car windows. They can also advantageously be used to clean other surfaces such as vinyl, Formica®, enamel, porcelain, wood, aluminum, steel, chrome, and the like. Applications include cleaning or refreshing countertops, indoor or outdoor furniture, upholstery, painted walls, wallpaper and floors. The specific use will largely depend on the benefits sought. For example, the mitts of the present invention provide an applicator for applying a disinfectant cleaner to a target surface and means to remove excess cleaner and debris. A mitt with barrier layers on both inner surfaces not only provides protection to the hand from the cleaning solution but also from the materials being cleaned from the target surface. Unlike conventional cleaning implements, the mitts are ideally suited for cleaning curved or other surfaces with jagged edges or tough to reach areas. As a result, the product form provides convenience not only because it comprises a substantially non-absorbent outer layer and another substantially absorbent for easy wetting, cleaning and buffing of surfaces, but also because it provides a means of doing the job on tough to reach areas or surfaces. Such a combination of benefits is lacking in present day cleaning systems. The mitts can be stored individually, or placed and stacked in containers, folded or unfolded. As such, they occupy little space and can be stored in small areas, which improves convenience for the users. The combination of easy storage and ability to clean tough to reach areas such as the interior of car windows, dashboards steering wheels and mirrors, makes them ideal for use in the car (glove compartment storage), where conventionally employed glass cleaning processes are awkward, ineffective and potentially hazardous.

Heating/Cooling

The mitt of the present invention may also include a heating and/or cooling element, also referred to as a temperature changing dement, such as shown in FIGS. 7–28. The heating/cooling element may for example, be located in the front panel 24 or the back panel 26. Other particular locations that the heating/cooling element may be located in the mitt are described in detail in United States Publication No. WO 01/26530 entitled "Semi-Enclosed Applicator for Distributing a Substage Onto a Target Surface" filed by Gruenbacher et al. on Oct. 10, 2000, which is incorporated by reference. The heating/cooling element may include an exothermic or endothentdc system that provides a heating or cooling effect, respectively. The systems may include heating/cooling by, but not limited to, an reactions, heats of solution, oxidation reactions, crystallization, corroding alloys, zeolite-liquid systems and/or heat of neutalizaton pH swings.

One embodiment of a heating/cooling element may include a solid-liquid or liquid-liquid heating/cooling system, such as an anhydrous reaction system, a heat of solution system, a zeolite system, an electro-chemical system, etc. A solid-liquid heating/cooling system includes any system in which an exothermic or endothermic change occurs during the combination or mixing of two or more components where at least one component is substantially liquid in nature (e.g., water) and at least one component is substantially solid in nature (e.g., anhydrous salts). A liquid-liquid heating/cooling system includes any system in which an exothermic or endothermic change occurs during the combination or mixing of two or more components where two or more of the components of the system are in a substantially liquid form.

Figure 9:
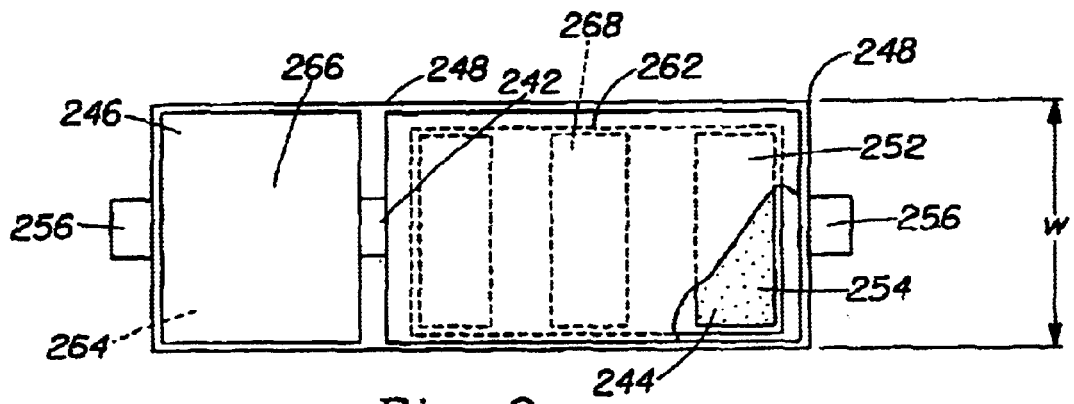
FIG. 9 is a top view of a temperature changing element of one embodiment of the present invention.
Figure 10:
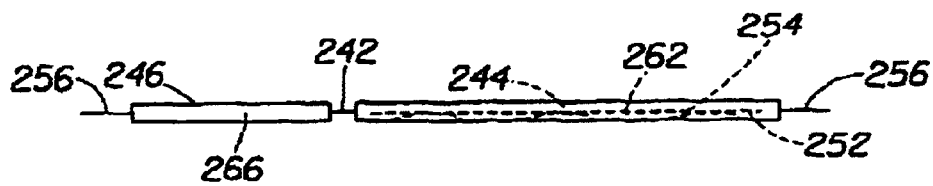
FIG. 10 is a side view of a temperature changing element of one embodiment of the present invention.
Figure 11:
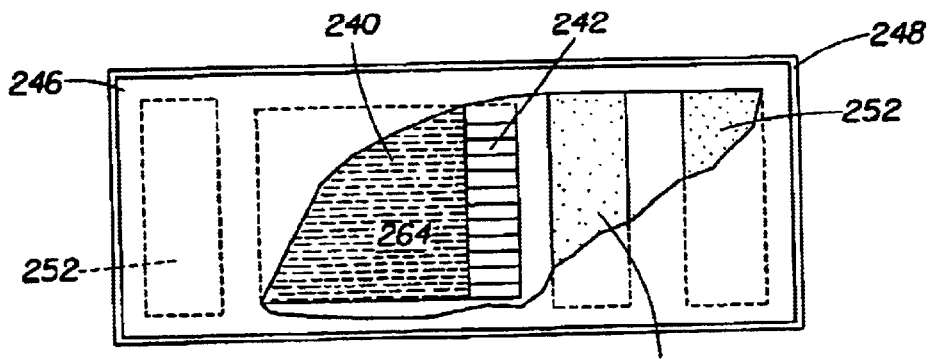
FIG. 11 is a top view of a temperature changing element of one embodiment of the present invention.
Figure 12:
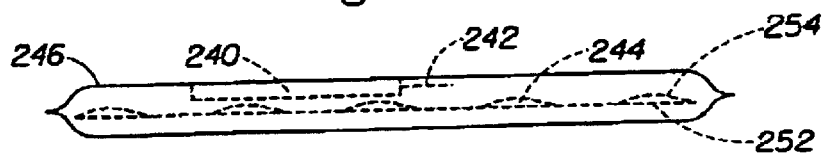
FIG. 12 is a side view of a temperature changing element of one embodiment of the present invention.

In one embodiment, the heating/cooling element may comprise a self-enclosed heating/cooling system. The heating/cooling system may include a substantially moisture impermeable outer layer 246, which may be at least partially flexible or deformable. For example, the moisture impermeable outer layer 246 may be a metallized film, foil laminate film, MYLAR®, a formed metal sheet or other water or moisture impermeable materials. The moisture impermeable outer layer 246 may also include a material having optimal thermal conductive parameters such as a metallized foil that permits greater thermal diffusivity and/or conductivity. The heating/cooling system may include at least two components of a solid-liquid or a liquid-liquid heating system housed within the moisture impermeable outer layer 246. The heating/cooling system, for example, may include a rupturable pouch 240 that contain(s) a first component of the heating/cooling system. The rupturable pouch may be formed from a metallized film or other material having a low moisture vapor transmission rate (MVTR) in order to minimize losses of the liquid component(s) contained within the pouch or entry of liquid or moisture into the pouch that may contaminate the solid component(s) contained within the pouch prior to activation of the heating/cooling element. The rupturable pouch 240 may include a frangible seal 242 to allow a user to rupture the seal by squeezing or otherwise applying pressure to the heating/cooling element and to release the first component from the rupturable pouch. Alternatively, the rupturable pouch may include weakened portions in the pouch material such as scores, perforations and the like, pull tabs, may include metal shavings or other items that may puncture the rupturable pouch upon the application of pressure, or may include any other means of rupturing a pouch known in the art. The heating/cooling element may also include a second component 244 of the heating/cooling system. The second component 244 may, for example, be contained loosely within the water impermeable outer layer 246 or, if a solid component, be contained within one or more porous, liquid permeable compartments 254 such as shown in FIGS. 9–12, 17, and 18. The liquid permeable compartments 254 may be formed by a porous material such as a porous cellulosic material (e.g., wet-laid or air-laid), a porous polymeric film such as a polyethylene film which has been needle-punched or vacuumed-formed, a polymeric mesh material such as a woven nylon mesh material such as Nitex™ supplied by Sefar America Inc., Depew, N.Y., etc. Preferably, the pore size of the porous material is smaller than the particles of the solid second component(s) 244. The heating/cooling element may include one or more compartments that house the solid second component(s) 244 located within the moisture impermeable outer layer 246. The solid second component(s) 244 may be packed within the one or more compartments of the heating/cooling element at a component volume in the range from about 60% to about 95% of the available compartment space in order to keep the solid second components in close proximity to each other. Tightly packing the solid second component(s) in one or more compartments can prevent the solid second component(s) from shifting in the heating/cooling element and can also prevent "saddle-bagging" of a flexible heating/cooling element Further, keeping the solid second component(s) in a packed state within one or more compartments can promote even heating/cooling in the heating/cooling element via a defined and repeatable amount of component per unit volume, can reduce the surface area exposure and thereby reduce the rapid surface convective losses of the heating/cooling element, and can better meter the rate that the heat produced or consumed by the exothermic or endothermic system due to forced conduction through the packed bed. In some embodiments, the pouch may further distribute any liquid component(s) across the surface of the solid second component(s) 244 through wicking and/or capillary action. Additionally, or in the alternative, a liquid distribution layer such as the layer 262 may be provided in proximity to the solid second component (s) 244 of the solid-liquid system to distribute any liquid component(s) across the surface of the solid second component(s) 244 through wicking and/or capillary action such as shown in FIGS. 9 and 10. This may be especially useful in embodiments where the solid second component(s) are contained in a porous sheet that will not readily wick the aqueous solution across its surface or in embodiments where the solid second components are contained loosely within the water impermeable outer layer 246. The liquid distribution layer, for example, may include a cellulosic material such as paper towel layers such as Bounty® sold by the Procter & Gamble Company of Cincinnati, Ohio, capillary channel fibers, hydrophilic woven and non-woven materials, apertured formed film or any other distribution materials known in the art. Further, absorbent, wicking or capillary action materials such as cellulosic materials, superabsorbent polymers and/or other hydroscopic materials may be interspersed within the particles of the solid second component(s) in order to allow for a more even dispersion of the liquid component(s) throughout the solid second component(s) allowing for full usage of the component(s). This may be especially useful in embodiments where the solid second component(s) are mixed with additives such as encapsulated phase change materials such as Thermasorb Series® available from Frisby Technologies, Winston-Salem, N.C. or polyethylene powders that are somewhat hydrophobic. Further, the addition of cellulosic materials may be beneficial in embodiments where another additive such as guar or xanthan gum is added to one or more of the component(s) to help tailor the temperature profile but may also affect the rate at which the reaction occurs due to a viscosity change in an aqueous solution liquid component. Further, the addition of cellulosic materials may also be beneficial where reactive materials such as magnesium sulfate or calcium chloride, in a packed form, may form a thin crystal sheet across the areas where the water first comes in contact with them. This may impede the progress of a liquid component to areas of the packed bed that are below the crystal surface.

Another embodiment of a heating/cooling element includes a solid-liquid and/or liquid-liquid heating/cooling system such as shown in FIGS. 9, 10, 13–16 and 19–22 in which multiple components of the system can be housed in adjacent chambers separated by a rupturable barrier 242 such as a frangible seal or other rupturable barrier such as described above. The heating/cooling element, for example, may include a water impermeable outer layer 246 formed into a pouch having two or more chambers that separately house at least a first component and a second component of the system prior to activation. Upon compression of one or more chambers of the heating/cooling element, the rupturable barrier 242 may burst and allow the first and second component(s) to come into contact with each other.

Figure 27:
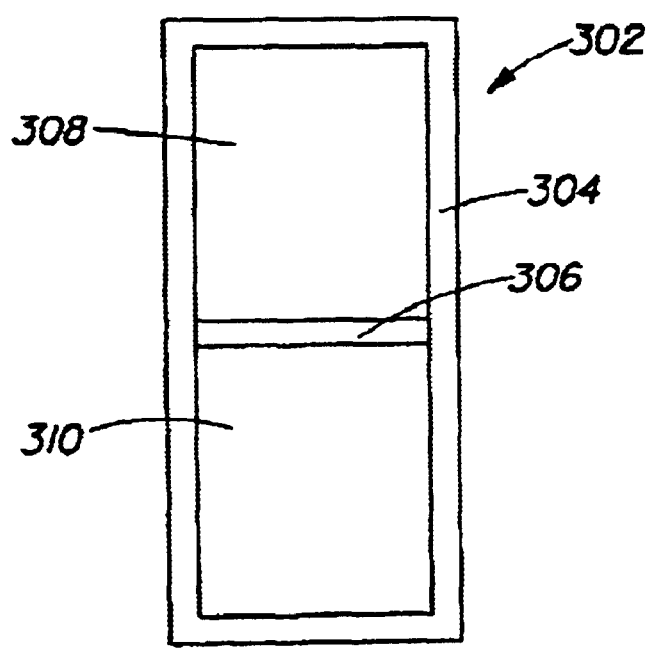
FIG. 27 is a plan view of one embodiment of a rupturable two component heating or cooling reservoir suitable for use in accordance with the present invention.
Figure 28:
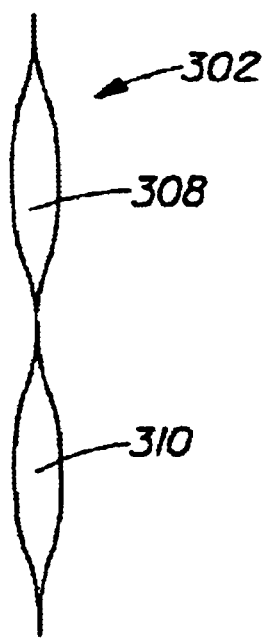
FIG. 28 is an elevational view of the rupturable heating or cooling reservoir of FIG. 27.

In one embodiment such as shown in FIG. 27, the heating element may include a pouch 302 having a permanent or strong seal 304 extending about at least a portion of the periphery of the pouch 302 (e.g., the pouch may include two or more pieces of film sealed around four sides, may include a film folded over itself and sealed around three sides, etc.). The pouch may include multiple chambers 308 and 310 that are separated by one or more frangible seals 306. In the embodiment shown in FIGS. 21 and 22, for example, the pouch may include a first chamber 268 and a second chamber 266 separated by a frangible seal 242. The first chamber 268 may contain a first component and the second chamber 266 may contain a second component. The fist and second components may include a solid component (e.g., anhydrous salt, electro-chemical alloys) and a liquid component (e.g., water), a liquid component and a solid component or a liquid component and a second liquid component Applying pressure to one or more of the chambers such as squeezing, pressing, kneading, etc. may rupture the frangible seal 242 and mix the components of the first and second chambers together to release or absorb energy from the environment.

Figure 8:
FIG. 8 is a side view of a temperature changing element of one embodiment of the present invention.
Figure 13:
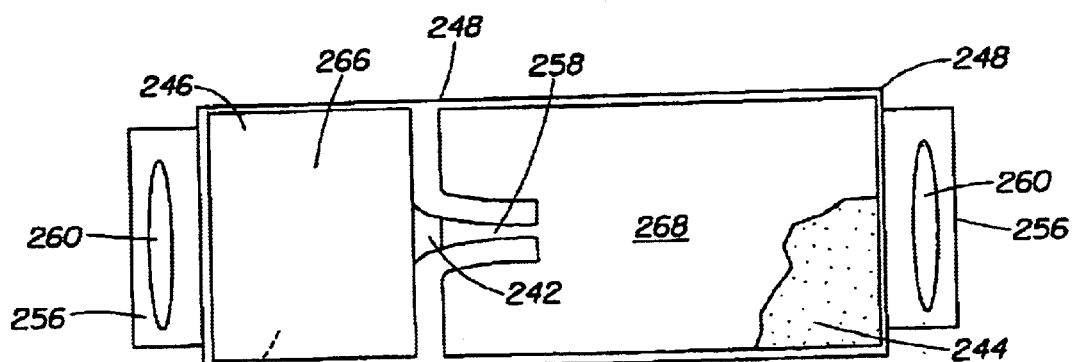
FIG. 13 is a top view of a temperature changing element of one embodiment of the present invention.
Figure 21:
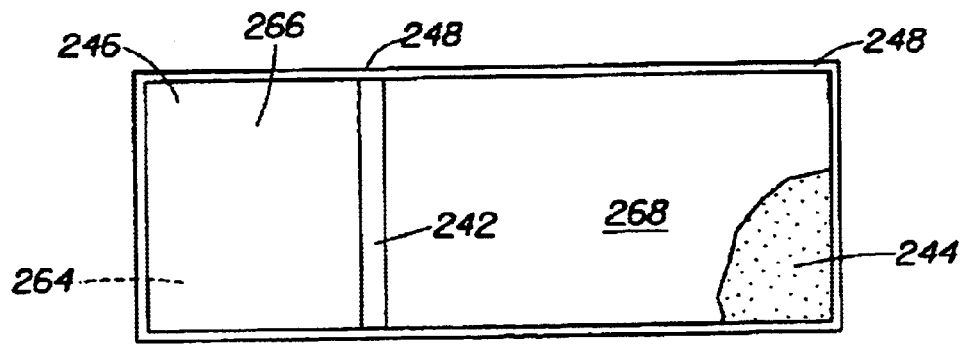
FIG. 21 is a top view of a temperature changing element of one embodiment of the present invention.
Figure 22:
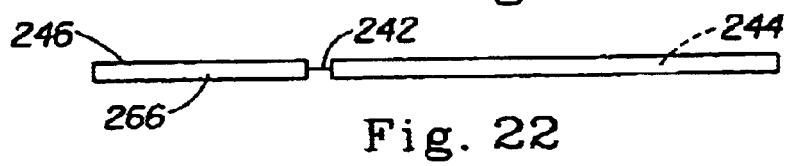
FIG. 22 is a side view of a temperature changing element of one embodiment of the present invention.

FIGS. 9, 10, 13 and 14, for example, show further embodiments of a heating/cooling element including a first component 264 housed in a first chamber 266 and a second component 244 housed in a second chamber 268 separated by a frangible seal 242. In these embodiments, a frangible seal 242 separates the first chamber 266 from the second chamber 268. The frangible seal 242 may extend a portion of the width W of the heating/cooling element such as shown in FIGS. 9, 10, 13 and 14 or may extend the entire width of the heating/cooling element between the first and the second chambers 266 and 268 such as shown in FIGS. 21 and 22. In one embodiment, the frangible seal may be designed narrowly such as shown in FIGS. 8, 13 and 15 to minimize the backflow of the first component 264 into the first chamber 266 after activation. Alternatively, or in addition, the heating/cooling element may also include a channel 258 such as shown in FIG. 13 that further restricts the backflow of the liquid component 264 into the first chamber 266 after activation. As shown in FIGS. 9, 10, 17 and 18, the heating/cooling element may also include a solid component housed in multiple compartments 252 and may be held in place by porous pouch 254. Alternatively, a solid component may be contained loosely within a chamber (e.g., the second component 244 shown in FIGS. 13–16, 21 and 22 may be a solid component contained loosely within the second chamber 268. The heating/cooling element may further comprise one or more attachment tabs 256 for attaching the heating/cooling element to structure of the mitt.

Figure 14:
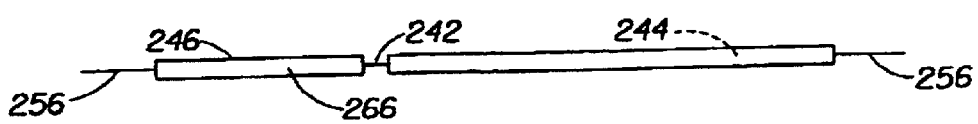
FIG. 14 is a side view of a temperature changing element of one embodiment of the present invention.
Figure 15:
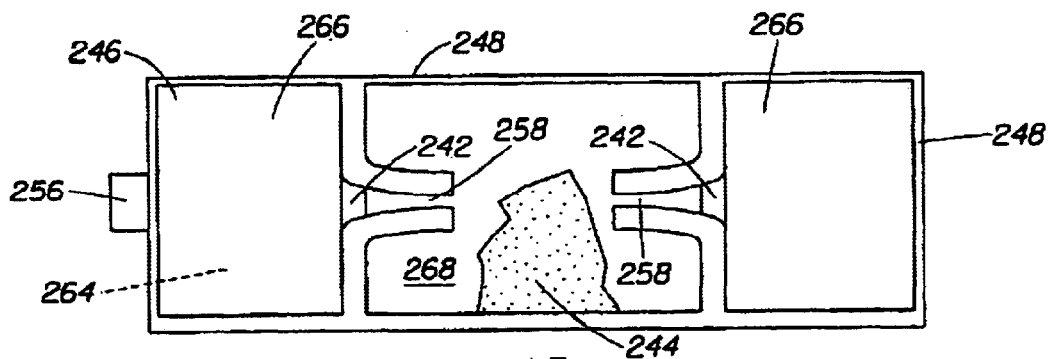
FIG. 15 is a top view of a temperature changing element of one embodiment of the present invention.

FIGS. 13 and 14 show yet another embodiment of a heating/cooling element that may be used in a solid-liquid or a liquid-liquid heating/cooling system. In this embodiment, a first liquid component can be housed in a first chamber 266 and a second liquid component or a solid component can be housed in a second chamber 268. The frangible seal 242 may extend across all or a portion of the width W of the heating cooling element, and channel 258 may extend into the second chamber 268 in order to prevent a backflow of the components into the first chamber 266 after activation.

Figure 16:
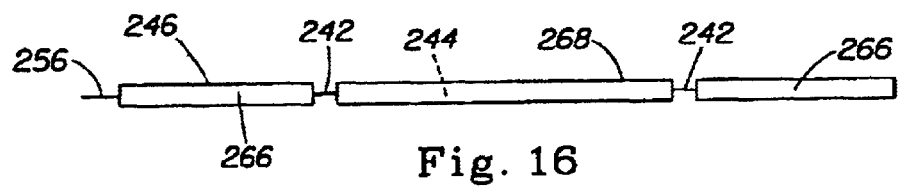
FIG. 16 is a side view of a temperature changing element of one embodiment of the present invention.

FIGS. 15 and 16 shows a temperature-changing element with at least two channels 258 that may be used for a substantially one-way flow of fluid components into the chamber 268. This allows for delivery of the fluid component to multiple locations within the chamber 268, which may be especially useful in larger packages or packages that may have varying orientations during activation such that wicking the liquid component(s) may become increasingly difficult.

Figure 17:
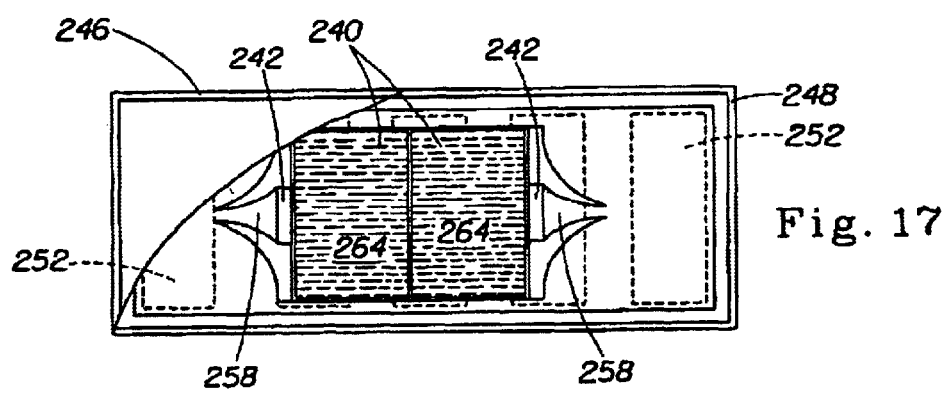
FIG. 17 is a top view of a temperature changing element of one embodiment of the present invention.
Figure 18:
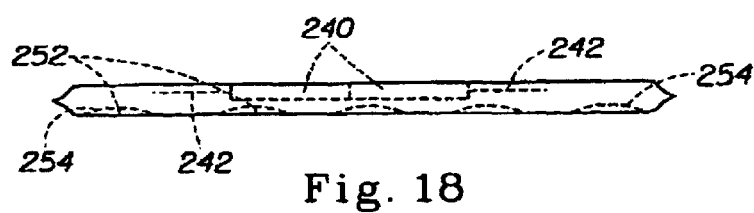
FIG. 18 is a side view of a temperature changing element of one embodiment of the present invention.

FIGS. 17 and 18 show a temperature-changing element in which a container 240 can be located above the reactant containing compartments 252. The figure also shows multiple exit channels 258 for the container 240. The compartments 252, for example, may be made of discrete packets in which one side is a porous material 254 and the other is a fluid impermeable film such as polyethylene. In the specific embodiment, the porous material 245 may be attached to the exterior package. This configuration disassociates the fluid bag from the heat generator and allows for the centralization of the fluid bag.

Figure 19:
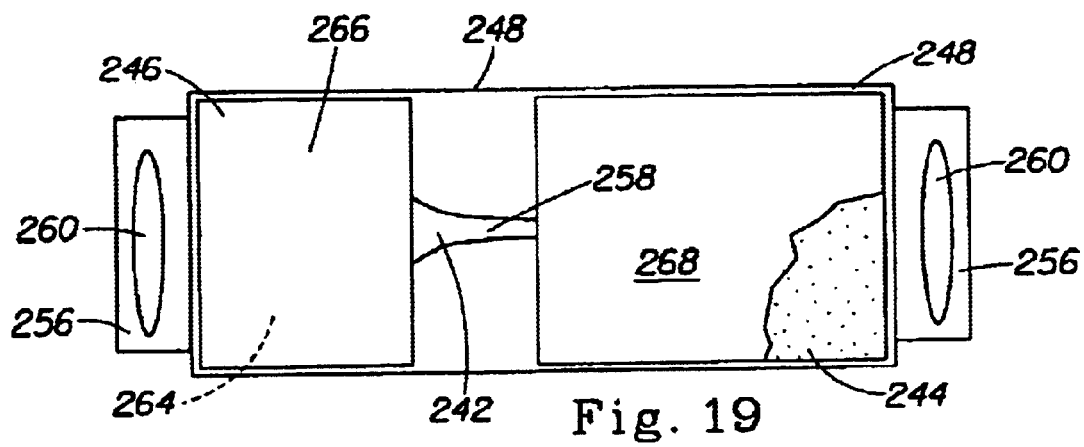
FIG. 19 is a top view of a temperature changing element of one embodiment of the present invention.
Figure 20:
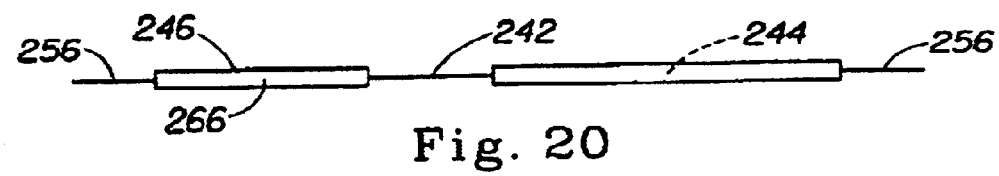
FIG. 20 is a side view of a temperature changing element of one embodiment of the present invention.

FIGS. 19 and 20 show an alternative embodiment of a temperature-changing element where the exit channel 258 is located within the seal area 248 to allow for the full use of the heating chamber. This may be beneficial for filling operations where channels extending into the chamber 268 may become an obstruction.

An exothermic solid-liquid heating system can include solid components such as calcium oxide, calcium carbonate, calcium sulfate, calcium chloride, cerous chloride, cesium hydroxide, sodium carbonate, ferric chloride, copper sulfate, magnesium sulfate, magnesium perchlorate, aluminum bromide, calcium aluminum hydride, aluminum chloride, sulfur trioxide (alpha form), zeolites (e.g. Carbsorb® 500 Series natural zeolite based on the mineral chabazite), mixtures thereof and other solid components of solid-liquid exothermic systems known in the art and combinations there of. An endothermic solid-liquid cooling system can include solid components such as sodium sulfate*$10H_2O$, sodium bicarbonate, potassium perchlorate, potassium sulfate potassium chloride, potassium chromate, urea, vanillin, calcium nitrate, ammonium nitrate, ammonium dichromate, ammonium chloride and other solid components of endothermic systems known in the art. These solid components may be in an anhydrous form and may be used such as in a powder, granular or prilled condition. These compounds are generally hydroscopic and dissolve in or react with a liquid component, such as water, and give off or absorb heat.

Further exothermic solid-liquid systems can include an electrochemical reaction including solid components such as iron, magnesium, aluminum, or combinations thereof that react in the presence of salt and water. In these embodiments, the liquid component may include a salt-water solution or may include water if salt is included with the solid component(s) 244.

Yet another solid-liquid or liquid-liquid exothermic system includes systems that use of heat of neutralization to give off heat using acid and base components such as citric acid having a pH of about 3 or 4 and calcium hydroxide having a pH of 12 in approximately a 2 to 1 ratio, respectively.

Figure 23:
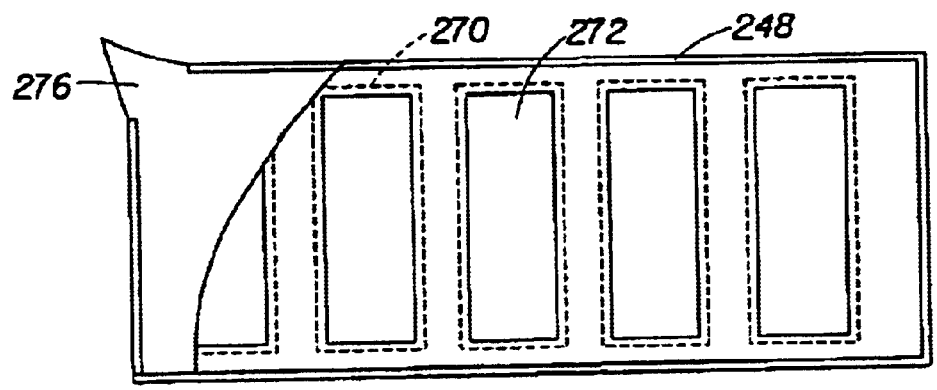
FIG. 23 is a top view of a temperature changing element of one embodiment of the present invention.
Figure 24:
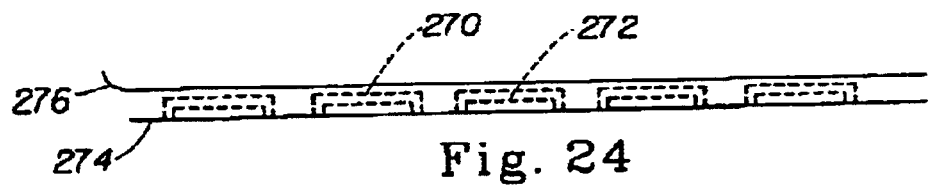
FIG. 24 is a side view of a temperature changing element of one embodiment of the present invention.

In another embodiment as shown in FIGS. 23 and 24, of a heating element may include a solid-gas heating system. A heating element may utilize the heat generated by supplying suitable amounts of water, salt, vermiculite, activated carbon and/or air to oxidize iron powder. For example, the heating element may include a porous bag 270, such as a fabric, an apertured film, etc., may allow oxygen-containing atmospheric gas to permeate into chamber that contains the solid component 272. The solid component 272, for example, may be filled with a uniform mixture of inorganic porous materials, iron powder, inorganic salts and water. The porous bag may further include a wetting agent and be capable of generating heat when exposed to the atmospheric air. This heating element may be formed by filling a mixture consisting of expanded inorganic porous materials such as vermiculite, iron powder, inorganic salts such as ammonium chloride and water containing a wetting agent into a porous fabric bag having air-permeability and sealing the bag. An example of solid-gas components is described in detail in U.S. Pat. No. 6,096,067 entitled "Disposable Thermal Body Pad" issued to The Procter and Gamble Company on Aug. 1, 2000, which is incorporated by reference.

FIGS. 23 and 24, for example, show a heating element including the solid component 272 of the solid/gas system. Thermal packs may further comprise a plurality of heat cells 272 spaced apart which provide controlled and sustained temperature and which reach their operating temperature range quickly. The heat cells can be embedded between the first 270 and the second 274 sides and fixedly attached within each thermal pack. The laminate structure may provide for oxygen permeability to each of the plurality of heat cells. Oxygen permeable layers such as known in the art, for example, may be located on the first side 270 of the laminate structure. The plurality of heat cells may have an oxygen activated, heat generating chemistry containing a mixture of powdered iron, powdered activated charcoal, vermiculite, water and salt. The second side of the structure may have an oxygen impermeable layer 274. The first side may further include an oxygen impermeable release layer 276 that can be removed to activate the heating system.

Figure 25:
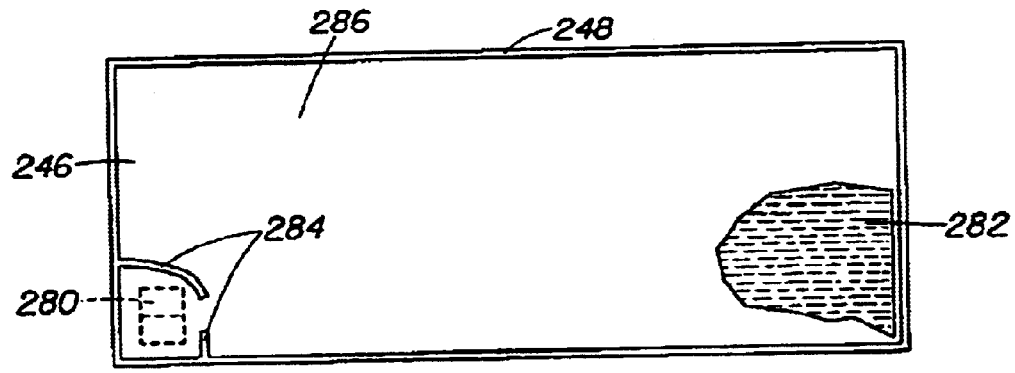
FIG. 25 is a top view of a temperature changing element of one embodiment of the present invention.
Figure 26:
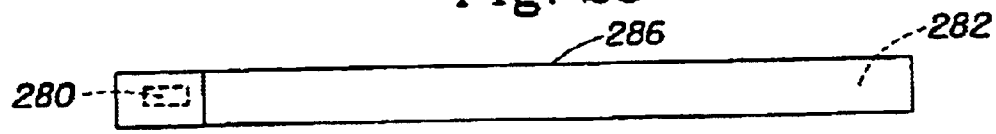
FIG. 26 is a side view of a temperature changing element of one embodiment of the present invention.

In another embodiment, FIGS. 25 and 26, of a heating element may include use of aqueous salt solution(s) supercooled so that the heat packs can be carried in the supercooled condition and activated with internal release of heat when desired. Sodium acetate, sodium thiosulfate and calcium nitrate tetrahydrate are examples of suitable salts.

FIGS. 25 and 26, for example, show a heating element comprising of the supercooled salt 282 in a pouch 286 with activator 280. To activate crystallization of solution 282 one can use the scraping of two metal pieces, the addition of additional crystals that comprise the solution, or any other activation method known in the art. As shown in FIG. 25, the activator 250 may be located in a corner of the pouch with restraining seals 284 holding it in an easily identifiable location. The solution 282, for example, may be 1:1 ratio by weight of sodium acetate and water mixed at an elevated temperature and cooled to ambient temperature in a super saturated state prior to activation.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable, semi-enclosed applicator for distributing a substance onto a target surface comprising a first side, a second side, and an internal cavity between said first and second sides, said applicator further having at least one opening such that said internal cavity is externally accessible, wherein:
  a. said first side comprises a porous sheet containing at least 50%, by weight, nonabsorbent material, said first side forming a plurality of rugosities;
  b. said second side comprises an absorbent sheet containing at least 50%, by weight, of cellulosic material;
  c. wherein said applicator further comprises a substantially fluid-impervious barrier layer within said internal cavity adjacent said first side; and
  d. wherein said applicator has a Ratio of Absorbency of said second side to said first side of at least about 1.5.

2. The applicator of claim 1, further comprising a second substantially fluid-impervious barrier layer adjacent said second side.

3. The applicator of claim 1, wherein said first side further includes a substantially absorbent layer located between said porous sheet and said barrier layer.

4. The applicator of claim 1, wherein said porous sheet comprises a fibrous nonwoven.

5. The applicator of claim 1, wherein said porous sheet comprises an aperture film.

6. The applicator of claim 1, wherein said absorbent sheet is a paper comprised of 100% natural cellulose fibers.

7. The applicator of claim 1, wherein said absorbent sheet is a fibrous nonwoven.

8. The applicator of claim 1, further comprising a friction-enhancing element located at least partially within said internal cavity during use.

9. The applicator of claim 1, further comprising a pocket located at least partially within said internal cavity.

10. The applicator of claim 1, further comprising a temperature-changing element.

11. A disposable, semi-enclosed applicator for distributing a substance onto a target surface comprising a first side, a second side, and an internal cavity between said first and second sides, said applicator further having at least one opening such that said internal cavity is externally accessible, wherein:
  a. said first side comprises a porous non-absorbent sheet having a basis weight of no greater than about 100 gsm;
  b. said second side comprises an absorbent sheet having a basis weight of no greater than about 140 gsm; and
  c. said applicator further comprises a substantially fluid-impervious barrier layer within said internal cavity adjacent said first side;
  said applicator having a Ratio of Absorbency of said second side to said first side of at least about 1.5.

12. The applicator of claim 11, wherein the Ratio of Absorbency of said second side to said first side is at least about 2.

13. The applicator of claim 12, wherein the Ratio of Absorbency of said second side to said first side is at least about 4.

14. The applicator of claim 11, wherein said first side has a basis weight of no greater than about 75 gsm, and said second side has a basis weight of no greater than about 120 gsm.

15. The applicator of claim 11, wherein said first side has a basis weight of no greater than about 55 gsm.

16. The applicator of claim 15, wherein the ratio of Absorbency of said second side to said first side is at least about 4.

17. The applicator of claim 11, further comprising a temperature changing element.

18. The applicator of claim 17, wherein said temperature changing element comprises a self-enclosed heating/cooling system.

19. The applicator of claim 11, wherein said barrier layer is extensible.

20. The applicator of claim 11, wherein said barrier layer is differentially extensible.

* * * * *

UNITED STATES PATENT AND TRADEMARK OFFICE
CERTIFICATE OF CORRECTION

PATENT NO. : 6,811,338 B1
DATED : November 2, 2004
INVENTOR(S) : Manske et al.

It is certified that error appears in the above-identified patent and that said Letters Patent is hereby corrected as shown below:

<u>Title page,</u>
Item [63], Related U.S Application Data, should read as follows:
-- [63] Continuation-in-part of application No. 09/451,536, filed on Dec. 1, 1999, now Pat. No. 6,508,602, which is a continuation-in-part of application No. 09,415,866, filed on Oct. 8, 1999 (now abandoned). --

Signed and Sealed this

Seventh Day of June, 2005

JON W. DUDAS
*Director of the United States Patent and Trademark Office*